United States Patent
Bang et al.

(10) Patent No.: US 8,859,767 B2
(45) Date of Patent: Oct. 14, 2014

(54) METHOD FOR PREPARING 1-(4-(4-(3,4-DICHLORO-2-FLUORO-PHENYLAMINO)-7-METHOXYQUIN-AZOLIN-6-YLOXY)PIPERIDIN-1-YL)-PROP-2-EN-1-ONE HYDROCHLORIDE AND INTERMEDIATES USED THEREIN

(71) Applicant: Hanmi Science Co., Ltd., Hwaseong-si (KR)

(72) Inventors: Keuk Chan Bang, Incheon (KR); Young Ho Moon, Suwon-si (KR); Young Kil Chang, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 0 days.

(21) Appl. No.: 14/349,887

(22) PCT Filed: Oct. 5, 2012

(86) PCT No.: PCT/KR2012/008077
§ 371 (c)(1),
(2), (4) Date: Apr. 4, 2014

(87) PCT Pub. No.: WO2013/051883
PCT Pub. Date: Apr. 11, 2013

(65) Prior Publication Data
US 2014/0275534 A1    Sep. 18, 2014

(30) Foreign Application Priority Data
Oct. 5, 2011 (KR) .......................... 10-2011-0101422

(51) Int. Cl.
C07D 239/94 (2006.01)
C07D 401/12 (2006.01)

(52) U.S. Cl.
CPC ............ *C07D 401/12* (2013.01); *C07D 239/94* (2013.01)
USPC ......................................................... 544/293

(58) Field of Classification Search
USPC ........................................................ 544/293
See application file for complete search history.

(56) References Cited

U.S. PATENT DOCUMENTS
2007/0135463 A1    6/2007   Himmelsbach et al.

FOREIGN PATENT DOCUMENTS
WO    2005/030765 A1    4/2005
WO    2008/150118 A2    12/2008
WO    2010/122340 A2    10/2010

OTHER PUBLICATIONS

International Searching Authority, International Search Report, PCT/KR2012/008077, dated Mar. 29, 2013.

*Primary Examiner* — Kristin Vajda
(74) *Attorney, Agent, or Firm* — Sughrue Mion, PLLC

(57) ABSTRACT

The present invention relates to an improved method for preparing 1-(4-(4-(3,4-dichloro-2-fluorophenylamino)-7-methoxyquinazolin-6-yloxy)piperidin-1-yl)-prop-2-en-1-one hydrochloride, which selectively and effectively inhibits the growth of cancer cells induced by over-expression of an epidermal growth factor receptor (EGFR) and prevents the development of drug resistance caused by mutation of a tyrosine kinase, and intermediates used therein.

18 Claims, No Drawings

METHOD FOR PREPARING 1-(4-(4-(3,4-DICHLORO-2-FLUOROPHENYL-AMINO)-7-METHOXYQUINAZOLIN-6-YLOXY) PIPERIDIN-1-YL)-PROP-2-EN-1-ONE HYDROCHLORIDE AND INTERMEDIATES USED THEREIN

CROSS-REFERENCE TO RELATED APPLICATIONS

This application is a National Stage of International Application No. PCT/KR2012/008077 filed Oct. 5, 2012, claiming priority based on Korean Patent Application No. 10-2011-0101422 filed Oct. 5, 2011, the contents of all of which are incorporated herein by reference in their entirety.

FIELD OF THE INVENTION

The present invention relates to an improved method for preparing 1-(4-(4-(3,4-dichloro-2-fluorophenylamino)-7-methoxyquinazolin-6-yloxy)piperidin-1-yl)-prop-2-en-1-one hydrochloride, which selectively and effectively inhibits the growth of cancer cells induced by over-expression of an epidermal growth factor receptor and prevents the development of drug resistance caused by mutation of a tyrosine kinase, and intermediates used therein.

BACKGROUND OF THE INVENTION 1-(4-(4-(3,4-dichloro-2-fluorophenylamino)-7-methoxyquinazolin-6-yloxy)piperidin-1-yl)-prop-2-en-1-one hydrochloride of formula (I) below is an important drug having antiproliferative activities such as anti-tumor activity, which can be used for selectively and effectively treating drug resistance caused by tyrosine kinase mutation. Its free base form, i.e., 1-(4-(4-(3,4-dichloro-2-fluorophenylamino)-7-methoxyquinazolin-6-yloxy)piperidin-1-yl)-prop-2-en-1-one having formula (II) below is identified as CAS Registry Number 1092364-38-9.

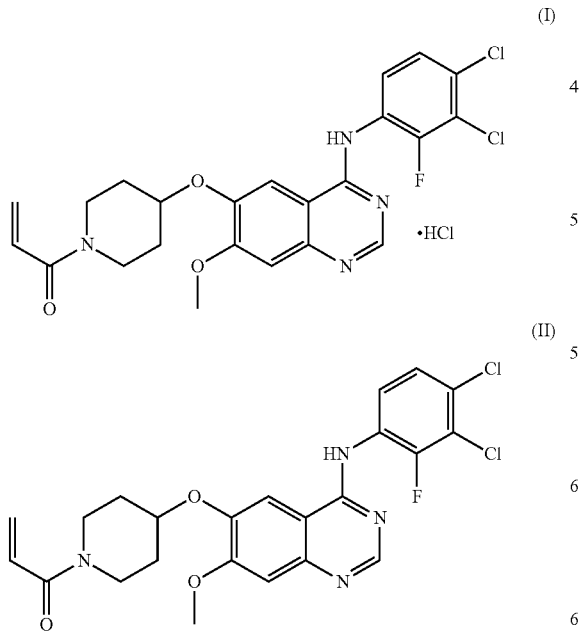

The compound of formula (II) may be prepared by, e.g., the method disclosed in Korean Patent No. 1013319, the reaction mechanism thereof being shown in Reaction Scheme 1 below. The compound of formula (II) prepared according to Reaction Scheme 1 may then be reacted with hydrochloric acid to produce the compound of formula (I).

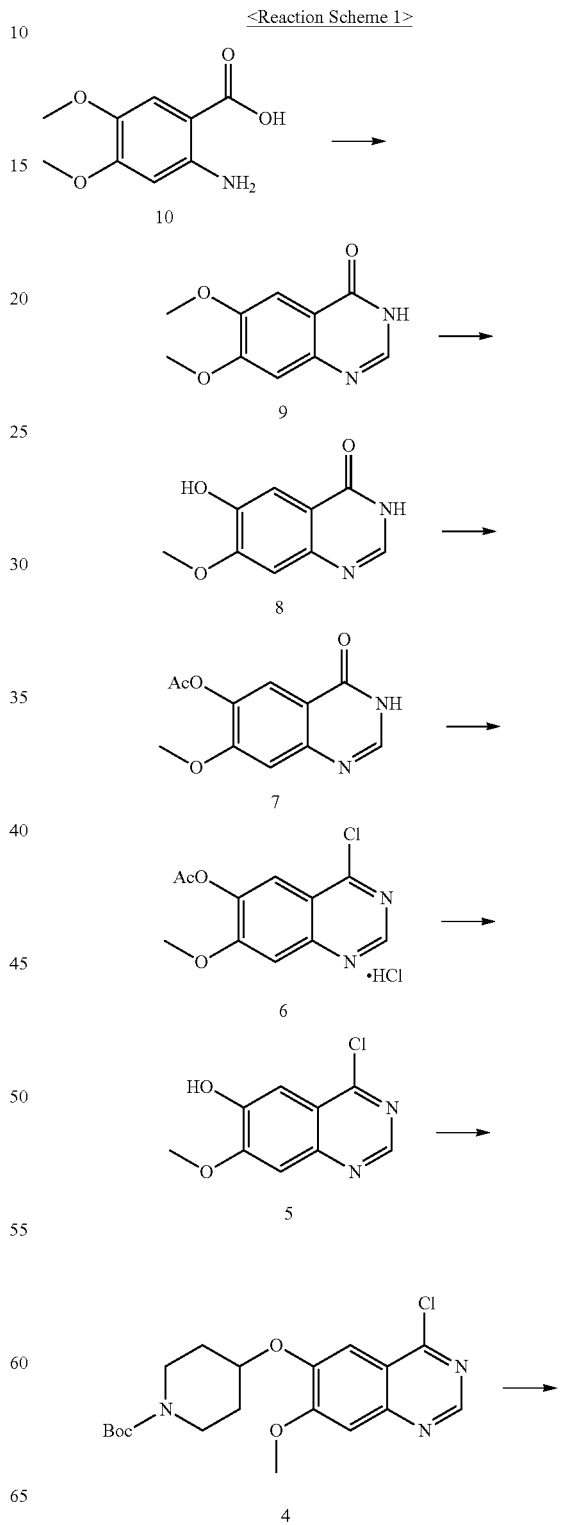

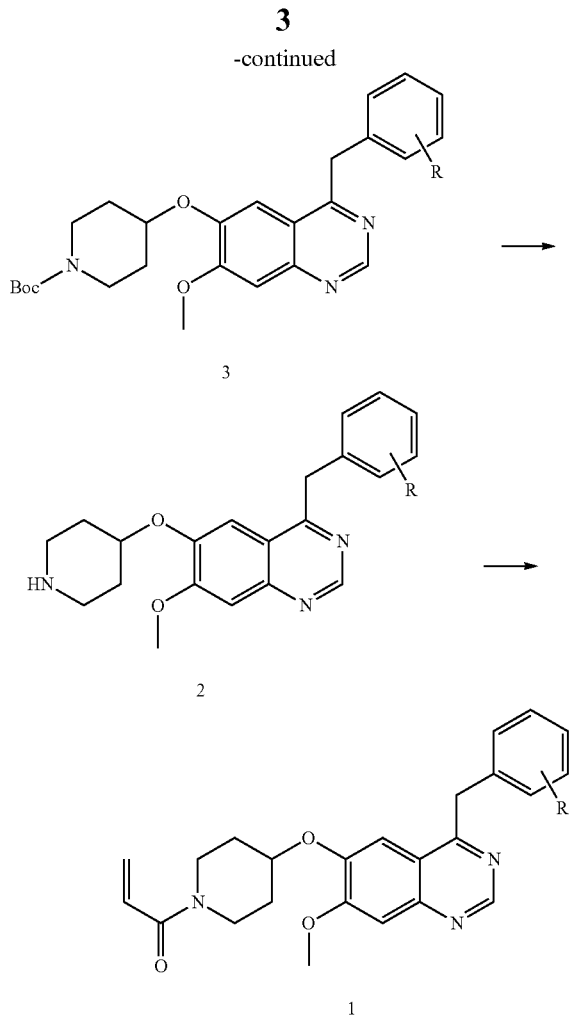

wherein R is halogen.

In Reaction Scheme 1, a compound of formula 10 is subjected to a condensation reaction with formamidine hydrochloride at a high temperature (e.g., 210° C.) to produce a compound of formula 9, which is then subjected to a reaction with L-methionine in an organic acid (e.g., methanesulfonic acid), whereby the methyl group at the position of C-6 of the compound of formula 9 is removed to produce a compound of formula 8.

Subsequently, the compound of formula 8 is subjected to a protection reaction in a base (e.g., pyridine) and anhydrous acetic acid to produce a compound of formula 7, which is then subjected to a reaction with an inorganic acid (e.g., thionyl-chloride or phosphorous oxychloride) in the presence of a catalytic amount of N,N-dimethylformamide under a reflux condition to produce a compound of formula 6 in hydrochlorate form.

The compound of formula 6 is added under stirring to an ammonia-containing alcohol solution (e.g., a 7N ammonia-containing methanol solution), whereby the acetyl group is removed to produce a compound of formula 5. The compound of formula 5 is subjected to the Mitsunobu reaction with tert-butyl 4-hydroxypiperidin-1-carboxylate to produce a compound of formula 4, which is then subjected to a substitution reaction with aniline in an organic solvent (e.g., 2-propanol or acetonitrile) to produce a compound of formula 3. Diisopropyl azodicarboxylate, diethyl azodicarboxylate or di-t-butyl azodicarboxylate, and triphenylphosphine may be employed for the Mitsunobu reaction. The compound of formula 3 is subjected to a reaction with an organic or inorganic acid (e.g., trifluoroacetic acid or heavy hydrochloric acid) in an organic solvent (e.g., dichloromethane), whereby the t-butoxycarbonyl group is removed to produce a compound of formula 2.

Subsequently, for the production of a compound of formula 1 (i.e., the compound of formula (II) of the present invention), the compound of formula 2 is subjected to an acylation reaction with acryloyl chloride in a mixture of an organic solvent (e.g., tetrahydrofuran) and water, or in dichloromethane, in the presence of an inorganic or organic base (e.g., sodium bicarbonate, pyridine or triethylamine). Alternatively, the compound of formula 2 is subjected to a condensation reaction with acrylic acid in the presence of a coupling agent (e.g., 1-ethyl-3-(3-dimethylaminopropyl)-carbodiimide (EDC) or 2-(1H-7-azabenzotriazol-1-yl)-1,1,3,3-tetramethyl europium hexafluorophosphate methanaminium (HATU)).

According to the above method, however, the step for preparing the compound of formula 9 is hazardous since it is conducted at a high temperature without a solvent, and the reaction may not proceed uniformly. Further, an excessive amount of thionyl chloride is used in the step for preparing the compound of formula 5, giving rise to difficulties in the subsequent steps. Hence, this method is not feasible for commercialization.

The main drawbacks of the above method for preparing the compound of formula (I) reside in that the yield of the final product in the acrylic reaction is very low (i.e., 13%) and that the reaction is accompanied by a number of side reactions, which requires a purification step by column chromatography. Also, when the compound of formula 3 is prepared by the Mitsunobu reaction, various by-products would be formed, which necessitates a purification step by column chromatography. Since expensive silica gel and an excessive amount of mobile phase solvents are required in such case, the above method is not feasible for commercialization.

Therefore, the present inventors have endeavored to develop a novel method for preparing the compound of formula (I) in high purity and yield, the method being economical and suitable for commercialization.

SUMMARY OF THE INVENTION

Accordingly, it is an object of the present invention to provide a method for preparing 1-(4-(4-(3,4-dichloro-2-fluorophenylamino)-7-methoxyquinazolin-6-yloxy)piperidin-1-yl)-prop-2-en-1-one hydrochloride.

It is another object of the present invention to provide intermediates used in preparing 1-(4-(4-(3,4-dichloro-2-fluorophenylamino)-7-methoxyquinazolin-6-yloxy)piperidin-1-yl)-prop-2-en-1-one hydrochloride.

In accordance with one aspect of the present invention, there is provided a method for preparing 1-(4-(4-(3,4-dichloro-2-fluorophenylamino)-7-methoxyquinazolin-6-yloxy)piperidin-1-yl)-prop-2-en-1-one hydrochloride of formula (I), which comprises the steps of:

(1) subjecting a compound of formula (VIII) to a reaction with a halogenating agent in the presence of an organic base, followed by a reaction with a compound of formula (X), to produce a compound of formula (VI);

(2) subjecting the compound of formula (VI) to a reaction with an ammonia solution in a polar protic solvent to produce a compound of formula (V);

(3) subjecting the compound of formula (V) to a reaction with a compound of formula (IX) in an inert polar protic solvent in the presence of a base to produce a compound of formula (IV);

(4) subjecting the compound of formula (IV) to a reaction with hydrochloric acid in an inert solvent to produce a compound of formula (III);

(5) subjecting the compound of formula (III) to an acrylation reaction with

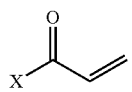

(wherein X is halogen) in the presence of a base to produce a compound of formula (II); and (6) subjecting the compound of formula (II) to a reaction with hydrochloric acid to produce the compound of formula (I):

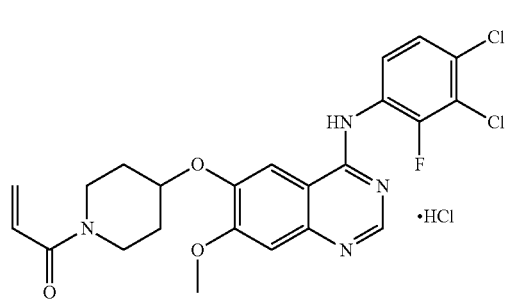

(I)
·HCl

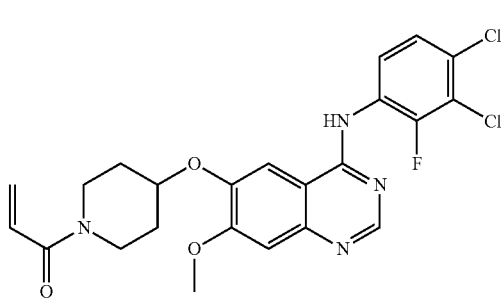

(II)

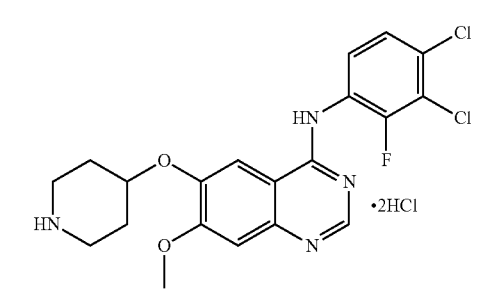

(III)
·2HCl

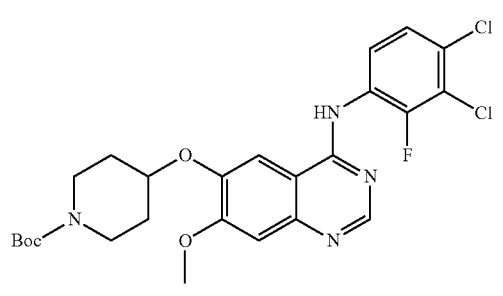

(IV)

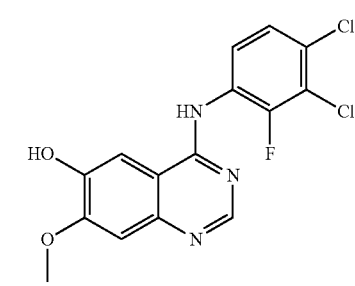

(V)

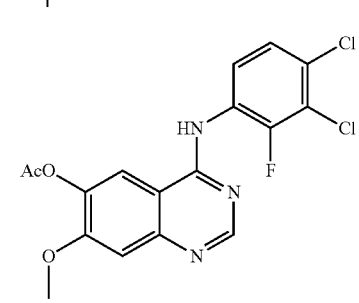

(VI)

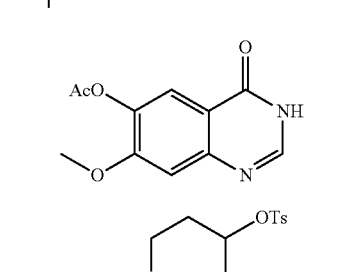

(VIII)

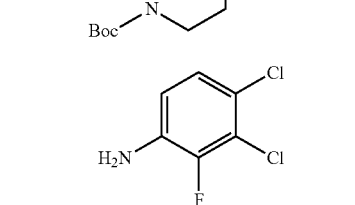

(IX)

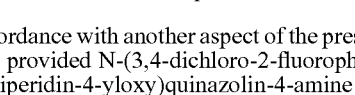

(X)

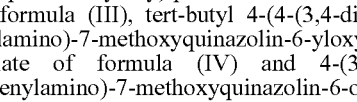

In accordance with another aspect of the present invention, there are provided N-(3,4-dichloro-2-fluorophenyl)-7-methoxy-6-(piperidin-4-yloxy)quinazolin-4-amine dihydrochloride of formula (III), tert-butyl 4-(4-(3,4-dichloro-2-fluorophenylamino)-7-methoxyquinazolin-6-yloxy)piperidin-1-carboxylate of formula (IV) and 4-(3,4-dichloro-2-fluorophenylamino)-7-methoxyquinazolin-6-ol of formula (V), which can be used as intermediates for preparing the compound of formula (I).

DETAILED DESCRIPTION OF THE INVENTION

The present method may be the carried out as shown in Reaction Schemes 2 to 6 below. Steps (1) and (2) of the present method can be carried out in accordance with Reaction Scheme 2:

<Reaction Scheme 2>

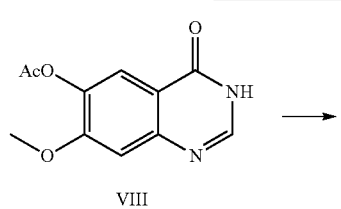

VIII

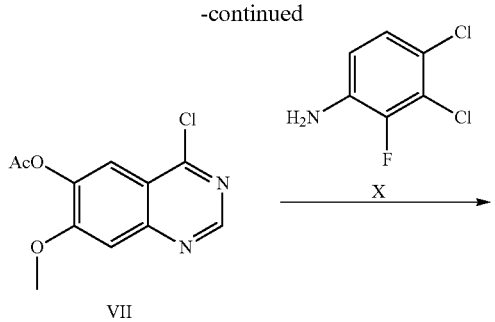

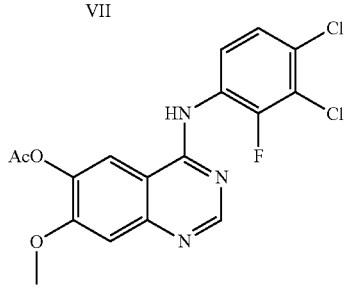

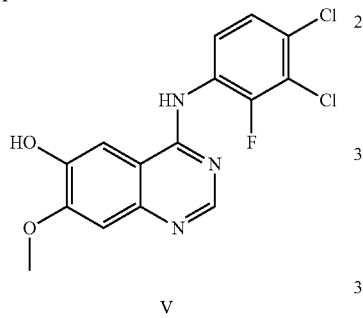

In Step (1), the compound of formula (VIII) as a starting material is subjected to a reaction with a halogenating agent in a solvent such as toluene or benzene in the presence of an organic base, followed by a reaction with the compound of formula (X), to produce 4-(3,4-dichloro-2-fluorophenylamino)-7-methoxyquinazolin-6-yl acetate of formula (VI).

The compound of formula (VIII) can be prepared by the method disclosed in Korean Patent No. 1013319.

The organic base used in Step (1) of the present method may be selected from the group consisting of diisopropylamine, triethylamine, diisopropyl ethylamine, diethylamine, pyridine, 4-dimethylpyridine, morpholine and a mixture thereof; and the halogenating agent may be selected from the group consisting of thionyl chloride, phosphorusoxy chloride and a mixture thereof.

The reaction may be conducted at a temperature of 50° C. to 150° C., preferably 60° C. to 90° C., more preferably about 75° C. As a result of the reaction with the halogenating agent, the compound of formula (VII) may be prepared as contained in the organic solvent, which cannot readily be separated. Subsequently, the compound of formula (VII) contained in the organic solvent is subjected to a reaction with the compound of formula (X) to produce 4-(3,4-dichloro-2-fluorophenylamino)-7-methoxyquinazolin-6-yl acetate of formula (VI).

In Step (2), the compound of formula (VI) prepared in Step (1) is subjected to a reaction with an ammonia solution or ammonia gas in a polar protic solvent (e.g., methanol, ethanol and propanol) at a temperature of 0° C. to 40° C., preferably 10° C. to 30° C., more preferably about 25° C., to produce 4-(3,4-dichloro-2-fluorophenylamino)-7-methoxyquinazolin-6-ol of formula (V).

In Step (3), as illustrated in Reaction Scheme 3, the compound of formula (V) is subjected to a reaction with tert-butyl 4-(tosyloxy)piperidin-1-carboxylate of formula (IX) in an inert polar protic solvent in the presence of a base to produce tert-butyl 4-(4-(3,4-dichloro-2-fluorophenylamino)-7-methoxyquinazolin-6-yloxy)piperidin-1-carboxylate of formula (IV).

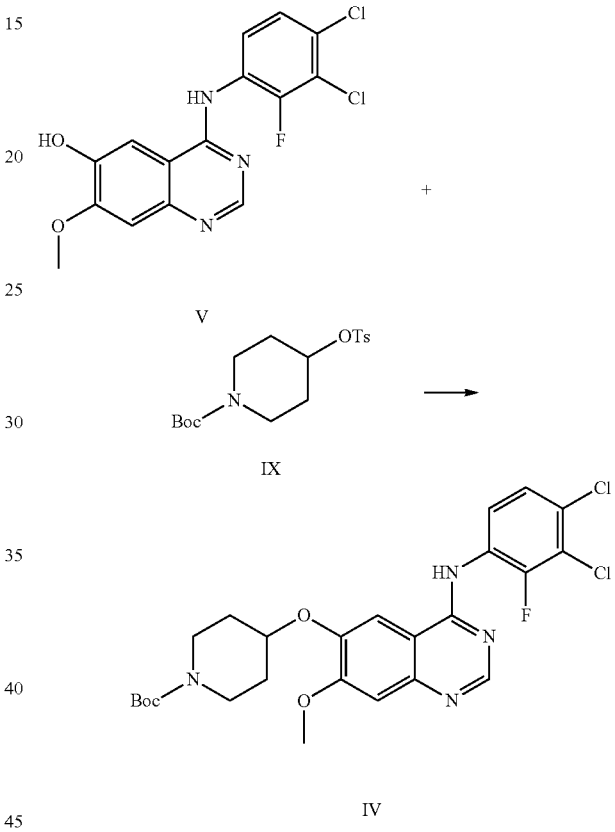

<Reaction Scheme 3>

The inert polar protic solvent used in Step (3) of the present method may be selected from the group consisting of N,N-dimethylformamide, N,N-dimethylacetamide, N-methylpyrrolidin-2-one, dimethyl sulfoxide and a mixture thereof. The base may be an alkali metal carbonate salt selected from the group consisting of sodium hydrogen carbonate, potassium carbonate, cesium carbonate and a mixture thereof. The base is used in an amount of 1 to 5 mole equivalents based on 1 mole equivalent of the compound of formula (V). The reaction may be conducted at a temperature of 60° C. to 100° C., preferably 70° C. to 90° C., more preferably about 80° C.

In accordance with one embodiment of the present invention, the compound of formula (IV) can be prepared in high purity and yield by simple recrystallization by $K_2CO_3$ in Step (3) of the present method. In contrast, according to the conventional method disclosed in Korean Patent No. 1013319, it is required to employ expensive diisopropyl azodicarboxylate (DIAD) as a main reagent and purify the product by column chromatography. Hence, the conventional method is not only uneconomical, but it is also ineffective as compared to the present method in terms of yield and purity (See Table 1).

TABLE 1

| | Main reagents* | | Purification method | Yield | Purity |
|---|---|---|---|---|---|
| Conventional method | DIAD | 1,300,000 KRW/kg | Column chromatography | 73% | 95% |
| Present method | $K_2CO_3$ | 61,000 KRW/kg | Recrystallization | 83% | >98% |

*Price based on Aldrich Handbook (2009-2010)

In Step (4), as depicted in Reaction Scheme 4, the compound of formula (IV) is subjected to a reaction with hydrochloric acid in an inert solvent to produce N-(3,4-dichloro-2-fluorophenyl)-7-methoxy-6-(piperidin-4-yloxy)quinazolin-4-amine dihydrochloride of formula (III).

<Reaction Scheme 4>

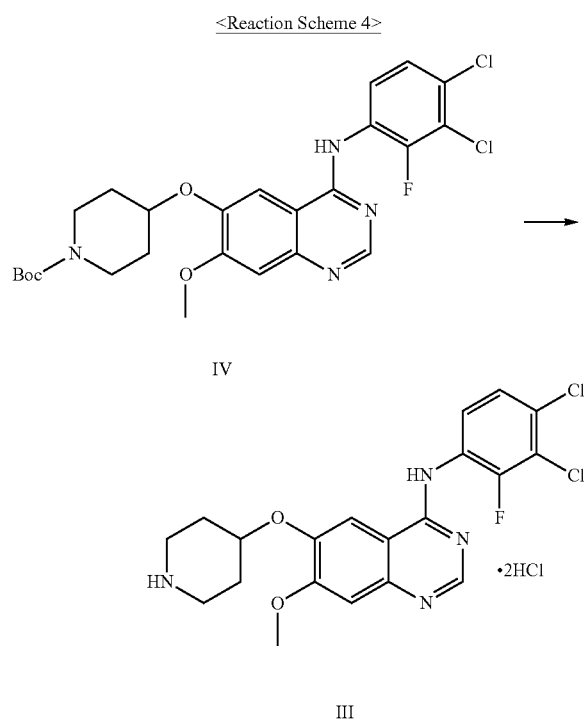

The inert solvent used in Step (4) of the present method may be selected from the group consisting of methanol, ethanol, propanol, ethyl acetate, methyl acetate, acetone and a mixture thereof. Hydrochloric acid may be used in an amount of 3 to 10 mole equivalents based on 1 mole equivalent of the compound of formula (IV). The reaction may be conducted under stirring for 1 to 24 hours at a temperature of 0° C. to 60° C., preferably 10° C. to 40° C., more preferably about 25° C.

In Step (5), as shown in Reaction Scheme 5, the compound of formula (III) is subjected to an acrylation reaction with

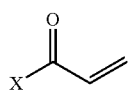

(wherein X is halogen), e.g., acryloyl chloride in the presence of a base to produce 1-(4-(4-(3,4-dichloro-2-fluorophenylamino)-7-methoxyquinazolin-6-yloxy)piperidin-1-yl)prop-2-en-1-one of formula (II).

<Reaction Scheme 5>

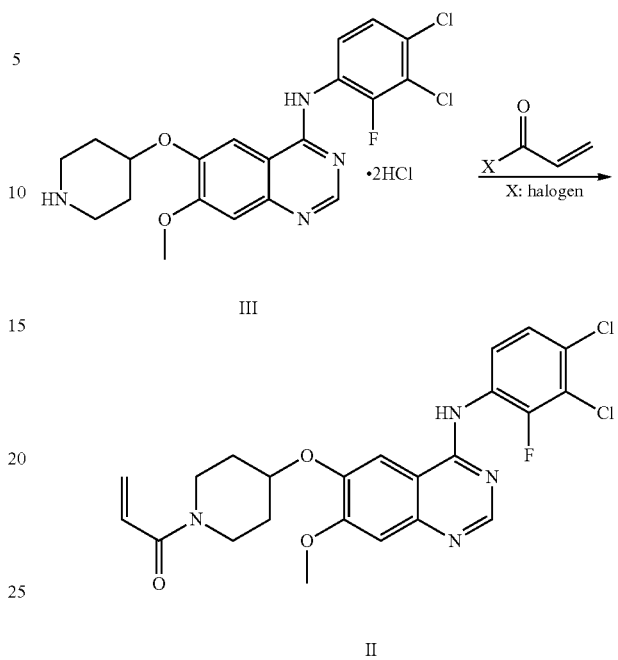

Step (5) of the present method can be conducted in an organic solvent such as tetrahydrofuran, ethyl acetate, acetone, 1,4-dioxane, acetonitrile, dichloromethane, carbon tetrachloride, chloroform, N,N-dimethyl formamide or dimethylsulfoxide, or in a mixture of said organic solvent and water. Preferred is a mixture of an organic solvent selected from the group consisting of tetrahydrofuran, ethyl acetate, acetone, 1,4-dioxane and acetonitrile, and water.

The base employed in Step (5) may be selected from the group consisting of an inorganic base such as sodium carbonate, calcium carbonate, potassium carbonate, sodium hydroxide, potassium hydroxide or cesium carbonate, or an organic base such as diisopropylamine, triethylamine, diisopropylethylamine or diethylamine. In this reaction, the base may be used in an amount of 3 to 5 mole equivalents based on 1 mole equivalent of the compound of formula (III). The acrylic reaction may be conducted under stirring for 20 minutes to 3 hours at a temperature of −30° C. to 20° C., preferably about 0° C.

Upon completion of the reaction, the resulting mixture is subjected to recrystallization with an aqueous acetone in an amount of 15 to 30 (w/v) times based on the amount of the compound of formula (III).

In accordance with one embodiment of the present invention, the compound of formula (II) can be prepared in high purity and yield by simple recrystallization in Step (5) of the present method. Meanwhile, according to the conventional method disclosed in Korean Patent No. 1013319, it requires purification of the product by column chromatography. Hence, the conventional method is ineffective as compared to the present method in terms of yield and purity (See Table 2).

TABLE 2

| | Purification method | Yield | Purity |
|---|---|---|---|
| Conventional method | Column chromatography | 13% | 95% |
| Present method | Recrystallization (aqueous acetone solution) | 75% | >98% |

In Step (6), as demonstrated in Reaction Scheme 6, the compound of formula (II) is subjected to a reaction with hydrochloric acid in an organic solvent to produce 1-(4-(4-(3,4-dichloro-2-fluorophenylamino)-7-methoxyquinazolin-6-yloxy)piperidin-1-yl)prop-2-en-1-one hydrochloride of formula (I).

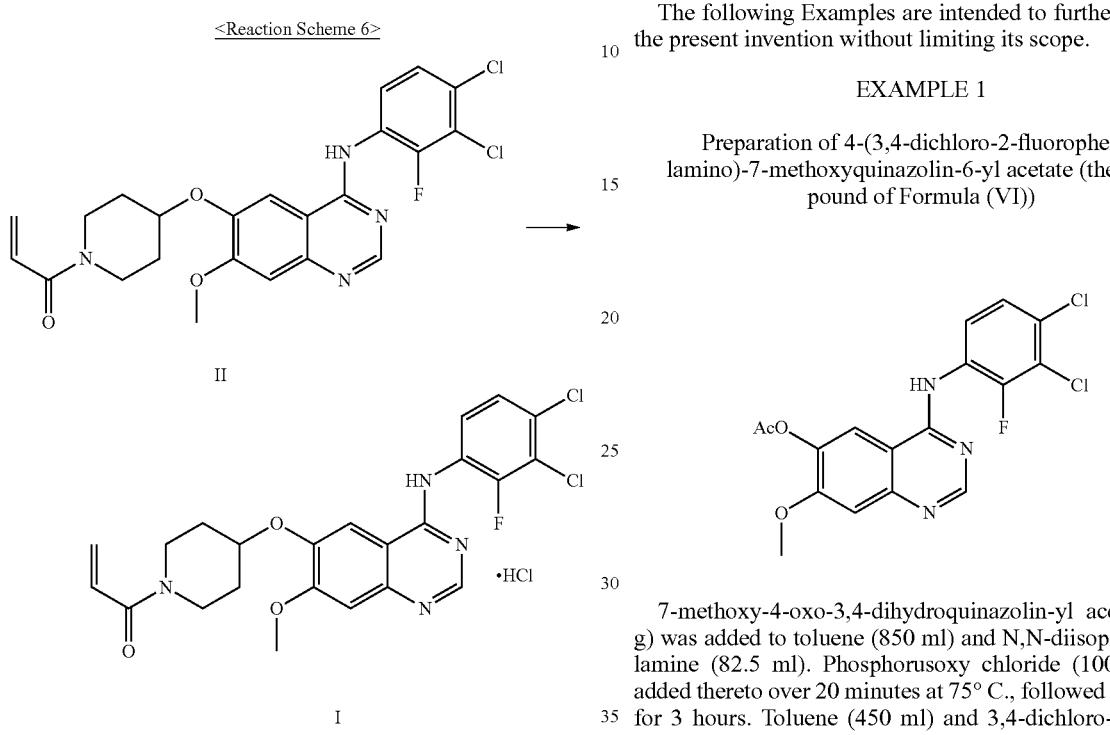

The organic solvent used in Step (6) of the present method may be selected from the group consisting of methanol, ethanol, propanol, isopropanol, butanol, ethyl acetate, acetone, tetrahydrofuran, acetonitrile, 1,4-dioxane and a mixture thereof. The reaction may be conducted at a temperature of 0° C. to 60° C., preferably 10° C. to 40° C., more preferably about 25° C.

In accordance with the present invention, there are provided such novel compounds as N-(3,4-dichloro-2-fluorophenyl)-7-methoxy-6-(piperidin-4-yloxy)quinazolin-4-amine dihydrochloride of formula (III), tert-butyl 4-(4-(3,4-dichloro-2-fluorophenylamino)-7-methoxyquinazolin-6-yloxy)piperidin-1-carboxylate of formula (IV), and 4-(3,4-dichloro-2-fluorophenylamino)-7-methoxyquinazolin-6-ol of formula (V)), which are the key intermediates used in the present method. These compounds can be used in preparing 1-(4-(4-(3,4-dichloro-2-fluorophenylamino)-7-methoxyquinazolin-6-yloxy)piperidin-1-yl)prop-2-en-1-one hydrochloride of formula (I), which selectively and effectively inhibits the growth of cancer cells induced by over-expression of an epidermal growth factor receptor and prevents the development of drug resistance caused by mutation of a tyrosine kinase.

In accordance with the present invention, the compounds of formulae (I) and (II) can be prepared in high yield by a simple and low cost method. According to the present method, the compound of formula (VIII) can simply be converted to the compound of formula (VI) in situ, and the compound of formula (V) can be produced without any special purification step. Also, the conventional method for preparing the compounds of formulae (II), (III) and (IV) necessitates an additional purification or extraction step by, e.g., column chromatography, which makes it less feasible for commercialization. However, the present method makes it possible to produce the final product in high purity and yield by adding a solvent to the reaction mixture to produce the product in solid phase and recrystallizing and filtering the product.

The following Examples are intended to further illustrate the present invention without limiting its scope.

EXAMPLE 1

Preparation of 4-(3,4-dichloro-2-fluorophenylamino)-7-methoxyquinazolin-6-yl acetate (the Compound of Formula (VI))

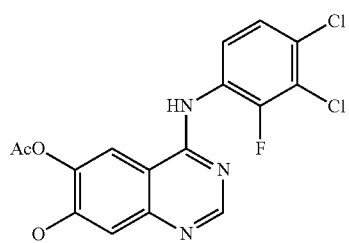

7-methoxy-4-oxo-3,4-dihydroquinazolin-yl acetate (100 g) was added to toluene (850 ml) and N,N-diisopropylethylamine (82.5 ml). Phosphorusoxy chloride (100 ml) was added thereto over 20 minutes at 75° C., followed by stirring for 3 hours. Toluene (450 ml) and 3,4-dichloro-2-fluoroaniline (84.6 g) were added to the resulting mixture, followed by stirring for 2 hours. Upon completion of the reaction, the resulting mixture was cooled to 25° C. The solid thus obtained was filtered under a reduced pressure and washed with toluene (400 ml). Isopropanol (1,000 ml) was added to the solid, which was then stirred for 2 hours. The resulting solid was filtered and washed with isopropanol (400 ml). The solid was dried at 40° C. in an oven to produce the compound of formula (VI) (143 g, yield: 83%).

$^1$H-NMR (DMSO-$d_6$, 300 MHz, ppm) δ 8.92 (s, 1H), 8.76 (s, 1H), 7.69-7.57 (m, 3H), 4.01 (s, 3H), 2.38 (s, 3H).

EXAMPLE 2

Preparation of 4-(3,4-dichloro-2-fluorophenylamino)-7-methoxyquinazolin-6-ol (the Compound of Formula (V))

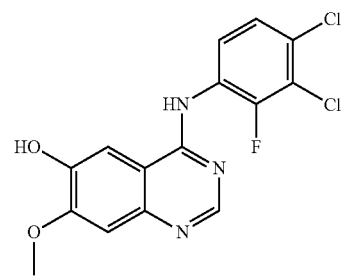 [SMILES: COc1cc2ncnc(Nc3ccc(Cl)c(Cl)c3F)c2cc1O]

4-(3,4-dichloro-2-fluorophenylamino)-7-methoxyquinazolin-6-yl acetate (100 g) was admixed with methanol (1,000 ml). The mixture was cooled to 10 to 15° C., added with an ammonia solution (460 g), and stirred for 3 hours at 25° C. The solid thus obtained was filtered and washed with a mixed solvent of methanol (200 ml) and water (200 ml). The resulting solid was dried at 40° C. in an oven to produce the compound of formula (V) (74 g, yield: 83%).

$^1$H-NMR (DMSO-$d_6$, 300 MHz, ppm) δ 9.57 (br, 2H), 8.35 (s, 1H), 7.68 (s, 1H), 7.61-7.52 (m, 2H), 7.21 (s, 1H), 3.97 (s, 3H).

EXAMPLE 3

Preparation of tert-butyl-4-(4-(3,4-dichloro-2-fluorophenylamino)-7-methoxyquinazolin-6-yloxy)piperidin-1-carboxylate (the Compound of Formula (IV))

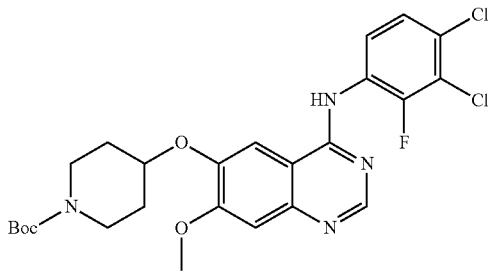 [SMILES: COc1cc2ncnc(Nc3ccc(Cl)c(Cl)c3F)c2cc1OC1CCN(C(=O)OC(C)(C)C)CC1]

4-(3,4-dichloro-2-fluorophenylamino)-7-methoxyquinazolin-6-ol (60 g) was admixed with N-dimethylformamide (360 ml) under stirring, followed by addition of tert-butyl 4-(tosyloxy)piperidin-1-carboxylate (120 g) and potassium carbonate (72 g) to the mixture. The reaction temperature was raised to 70° C., and the mixture was stirred for 14 hours. The temperature of the resulting solution was cooled to 25° C., and water (480 ml) was slowly added thereto. The solid thus obtained was filtered and dried. The solid was dissolved in a mixed solvent (600 ml) of dichloromethane and methanol. Active carbon (6 g) was then added thereto, followed by stirring for 30 minutes. The resulting mixture was filtered through a Celite pad, distilled under a reduced pressure, added with acetone (300 ml), and stirred for 2 hours. The resulting solid was filtered and washed with acetone (100 ml). The solid was dried at 40° C. in an oven to produce the compound of formula (IV) (75 g, yield: 83%).

$^1$H-NMR (DMSO-$d_6$, 300 MHz, ppm) δ 8.69 (s, 1H), 8.47 (t, 1H), 7.34-7.29 (m, 2H), 7.20 (s, 1H), 4.63-4.60 (m, 1H), 3.82 (s, 3H), 3.83-3.76 (m, 2H), 3.37-3.29 (m, 2H), 1.99-1.96 (m, 2H), 1.90-1.84 (m, 2H), 1.48 (s, 9H).

EXAMPLE 4

Preparation of N-(3,4-dichloro-2-fluorophenyl)-7-methoxy-6-(piperidin-4-yloxy)quinazolin-4-amine dihydrochloride (the Compound of Formula (III))

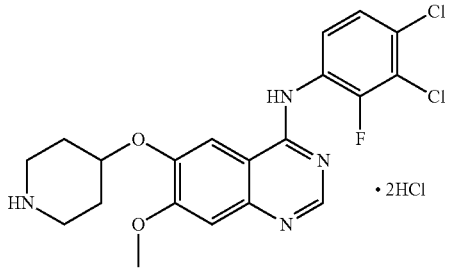 [SMILES: COc1cc2ncnc(Nc3ccc(Cl)c(Cl)c3F)c2cc1OC1CCNCC1]

Acetone (740 ml) was added to tert-butyl 4-(4-(3,4-dichloro-2-fluorophenylamino)-7-methoxyquinazolin-6-yloxy)piperidin-1-carboxylate (75 g), which was then stirred. The mixture was added with hydrochloric acid (145 ml) for 10 minutes and stirred for 5 hours. Upon completion of the reaction, the resulting mixture was filtered, and the solid thus obtained was washed with acetone (73 ml). The solid was dried at 30° C. in an oven to produce the compound of formula (III) (71 g, yield: 99%).

$^1$H-NMR (DMSO-$d_6$, 300 MHz, ppm) δ2.95 (bs, 1H), 9.42 (bs, 1H), 9.18 (bs, 1H), 9.01 (s, 1H), 8.86 (s, 1H), 7.69-7.56 (m, 2H), 7.45 (s, 1H), 5.11-5.08 (m, 1H), 4.03 (s, 3H), 3.29-3.20 (m, 4H), 2.33-2.30 (m, 2H), 1.96-1.93 (m, 2H).

EXAMPLE 5

Preparation of 1-(4-(4-(3,4-dichloro-2-fluorophenylamino)-7-methoxyquinazolin-6-yloxy)piperidin-1-yl)prop-2-en-1-one (the Compound of Formula (II))

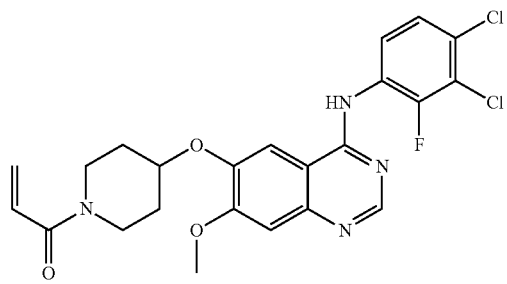

N-(3,4-dichloro-2-fluorophenyl)-7-methoxy-6-(piperidin-4-yloxy)quinazolin-4-amine dihydrochloride (100 g) and sodium hydrogen carbonate (66 g) were added to a mixed solvent of tetrahydrofuran (630 ml) and water (1 L), and the temperature of the reaction mixture was cooled to 0° C. with iced water. Acryloyol chloride (24 ml) diluted with tetrahydrofuran (370 ml) was slowly added to the reaction mixture over 30 minutes, followed by stirring at 0° C. for 30 minutes. Upon completion of the reaction, aqueous acetone (2.0 L) was added to the resulting mixture, which was stirred for 12 hours and filtered to produce 1-(4-(4-(3,4-dichloro-2-fluorophenylamino)-7-methoxyquinazolin-6-yloxy)piperidin-1-yl)prop-2-en-1-one (72 g, yield: 75%). The solid thus obtained was dissolved in a mixed solvent of dichloromethane (200 ml) and methanol (100 ml), added with ethyl acetate (1.2 L), and stirred for 12 hours. The resulting solid was filtered and washed with ethyl acetate (100 ml). The solid was dried at 40° C. in an oven to produce the compound of formula (II) (55 g, yield: 76%, total yield=57%).

$^1$H-NMR (CDCl$_3$, 300 MHz, ppm) δ8.68 (s, 1H), 8.39 (t, 3H), 7.31 (m, 3H), 6.61 (m, 1H), 6.29 (m, 1H), 5.72 (m, 1H), 4.75 (m, 1H), 4.02 (s, 3H), 3.89 (m, 2H), 3.60 (m, 2H), 1.86 (m, 4H).

EXAMPLE 6

Preparation of 1-(4-(4-(3,4-dichloro-2-fluorophenylamino)-7-methoxyquinazolin-6-yloxy)piperidin-1-yl)prop-2-en-1-one hydrochloride (the Compound of Formula (I))

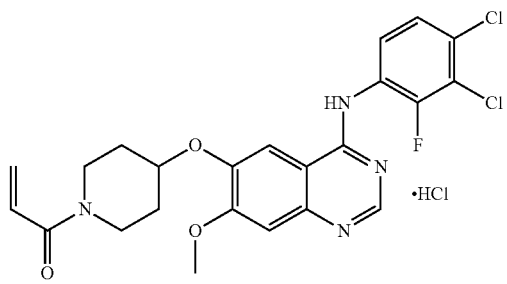 [SMILES: C=CC(=O)N1CCC(Oc2cc3c(Nc4ccc(Cl)c(Cl)c4F)ncnc3cc2OC)CC1 ; Cl]

1-(4-(4-(3,4-dichloro-2-fluorophenylamino)-7-methoxyquinazolin-6-yloxy)piperidine-1-yl)prop-2-en-1-one (150 g) was added to methanol (700 ml). Hydrochloric acid (38.2 ml) diluted with methanol (300 ml) was added thereto, followed by stirring for 24 hours. The solid thus obtained was filtered and washed with acetone (100 ml). The resulting solid was dried at 40° C. in an oven for 24 hours to produce the compound of formula (I) (131 g, yield: 81%).

$^1$H-NMR (DMSO-d$_6$, 300 MHz, ppm) δ2.31 (bs, 1H), 8.83 (s, 1H), 8.67 (s, 1H), 7.64-7.55 (m, 2H), 7.39 (s, 1H), 6.87-6.78 (m, 1H), 6.12-6.06 (m, 1H), 5.68-5.64 (m, 1H), 5.07-5.01 (m, 1H), 4.06-3.88 (m, 5H), 3.51 (t, 1H), 3.32 (t, 1H), 2.10 (t, 1H), 1.60 (t, 1H).

While the invention has been described with respect to the above specific embodiments, it should be recognized that various modifications and changes may be made to the invention by those skilled in the art which also fall within the scope of the invention as defined by the appended claims.

What is claimed is:

1. A method for preparing a 1-(4-(4-(3,4-dichloro-2-fluorophenylamino)-7-methoxyquinazolin-6-yloxy)piperidin-1-yl)-prop-2-en-1-one hydrochloride of formula (I), which comprises the steps of:
   (1) subjecting a compound of formula (VIII) to a reaction with a halogenating agent in the presence of an organic base, followed by a reaction with a compound of formula (X), to produce a compound of formula (VI);
   (2) subjecting the compound of formula (VI) to a reaction with an ammonia solution in a polar protic solvent to produce a compound of formula (V);
   (3) subjecting the compound of formula (V) to a reaction with a compound of formula (IX) in an inert polar protic solvent in the presence of a base to produce a compound of formula (IV);
   (4) subjecting the compound of formula (IV) to a reaction with hydrochloric acid in an inert solvent to produce a compound of formula (III);
   (5) subjecting the compound of formula (III) to an acrylation reaction with

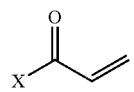

(wherein X is halogen) in the presence of a base to produce a compound of formula (II); and
   (6) subjecting the compound of formula (II) to a reaction with hydrochloric acid to produce the compound of formula (I):

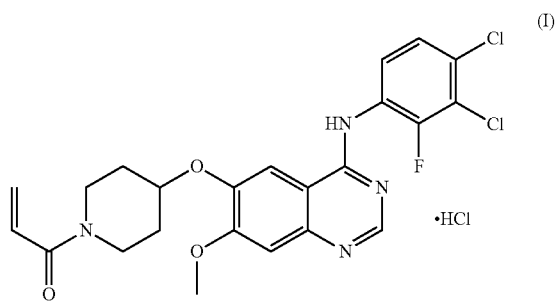 [SMILES: C=CC(=O)N1CCC(Oc2cc3c(Nc4ccc(Cl)c(Cl)c4F)ncnc3cc2OC)CC1 ; Cl]

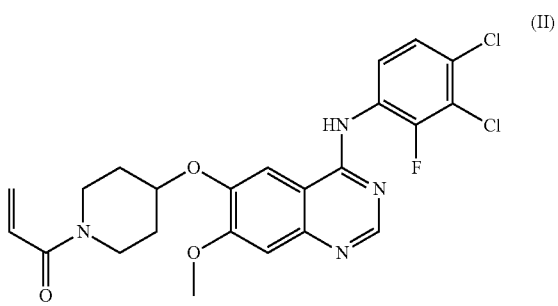

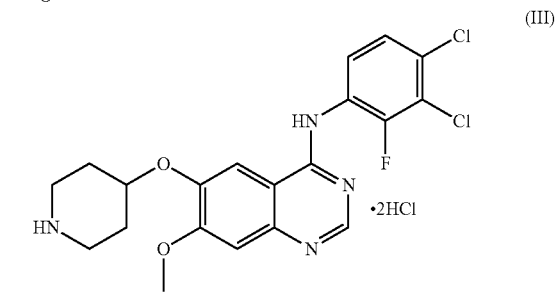

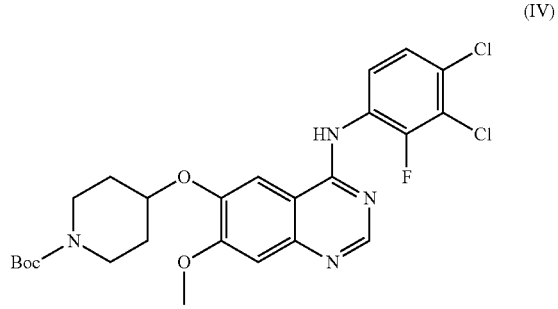

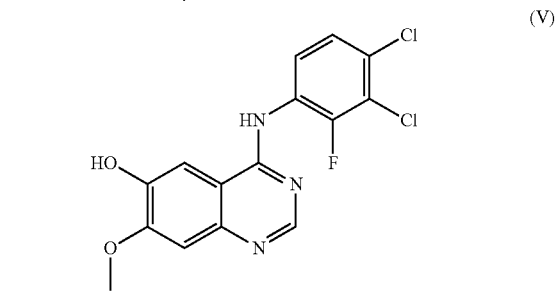

-continued

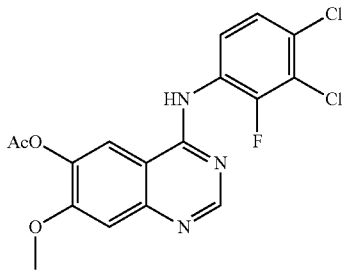
(VI)

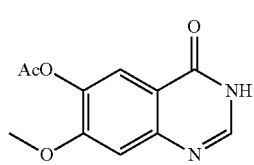
(VIII)

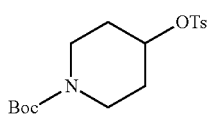
(IX)

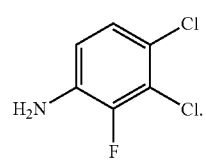
(X)

2. The method of claim 1, wherein Step (1) is conducted in a solvent selected from the group consisting of toluene, benzene and a mixture thereof.

3. The method of claim 1, wherein said organic base in Step (1) is selected from the group consisting of diisopropylamine, triethylamine, diisopropyl ethylamine, diethylamine, pyridine, 4-dimethylpyridine, morpholine and a mixture thereof.

4. The method of claim 1, wherein said halogenating agent in Step (1) is selected from the group consisting of thionyl chloride, phosphorusoxy chloride and a mixture thereof.

5. The method of claim 1, wherein said polar protic solvent in Step (2) is selected from the group consisting of methanol, ethanol, propanol and a mixture thereof.

6. The method of claim 1, wherein said inert polar protic solvent in Step (3) is selected from the group consisting of N,N-dimethylformamide, N,N-dimethylacetamide, N-methylpyrrolidin-2-one, dimethyl sulfoxide and a mixture thereof.

7. The method of claim 1, wherein said base in Step (3) is an alkali metal carbonate salt selected from the group consisting of sodium hydrogen carbonate, potassium carbonate, cesium carbonate and a mixture thereof.

8. The method of claim 7, wherein said base is employed in an amount of 1 to 5 mole equivalents based on 1 mole equivalent of the compound of formula (V).

9. The method of claim 1, wherein said inert solvent in Step (4) is selected from the group consisting of methanol, ethanol, propanol, ethyl acetate, methyl acetate, acetone and a mixture thereof.

10. The method of claim 1, wherein said hydrochloric acid in Step (4) is employed in an amount of 3 to 10 mole equivalents based on 1 mole equivalent of the compound of formula (IV).

11. The method of claim 1, wherein Step (5) is conducted in an organic solvent selected from the group consisting of tetrahydrofuran, ethyl acetate, acetone, 1,4-dioxane, acetonitrile, dichloromethane, carbon tetrachloride, chloroform, N,N-dimethyl formamide and dimethylsulfoxide, or a mixture of said organic solvent and water.

12. The method of claim 1, wherein said base in Step (5) is selected from the group consisting of sodium carbonate, calcium carbonate, potassium carbonate, sodium hydroxide, potassium hydroxide, cesium carbonate, diisopropylamine, triethylamine, diisopropylethylamine and diethylamine.

13. The method of claim 1, wherein said base in Step (5) is employed in an amount of 3 to 5 mole equivalents based on 1 mole equivalent of the compound of formula (III).

14. The method of claim 1, wherein Step (5) further comprises subjecting the compound of formula (II) to recrystallization with an aqueous acetone in an amount of 15 to 30 (w/v) times based on the amount of the compound of formula (III).

15. The method of claim 1, wherein Step (6) is conducted in an organic solvent selected from the group consisting of methanol, ethanol, propanol, isopropanol, butanol, ethyl acetate, acetone, tetrahydrofuran, acetonitrile, 1,4-dioxane and a mixture thereof.

16. N-(3,4-dichloro-2-fluorophenyl)-7-methoxy-6-(piperidin-4-yloxy)quinazolin-4-amine dihydrochloride of formula (III):

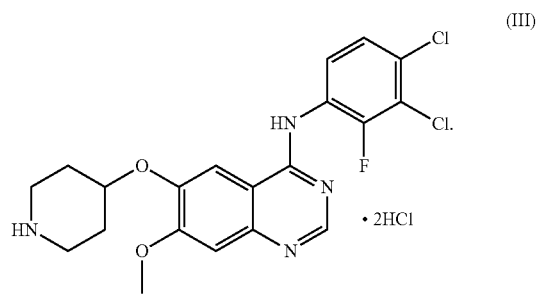 [SMILES: COc1cc2ncnc(Nc3ccc(Cl)c(Cl)c3F)c2cc1OC1CCNCC1]
(III)

17. tert-butyl 4-(4-(3,4-dichloro-2-fluorophenylamino)-7-methoxyquinazolin-6-yloxy)piperidin-1-carboxylate of formula (IV):

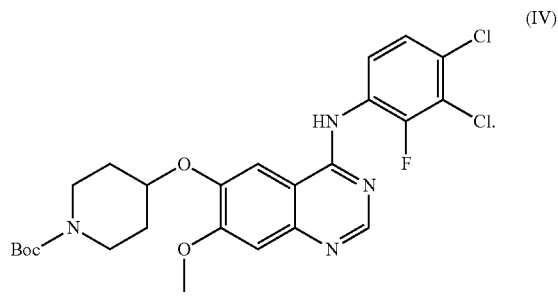 [SMILES: COc1cc2ncnc(Nc3ccc(Cl)c(Cl)c3F)c2cc1OC1CCN(C(=O)OC(C)(C)C)CC1]
(IV)

18. 4-(3,4-dichloro-2-fluorophenylamino)-7-methoxyquinazolin-6-ol of formula (V):
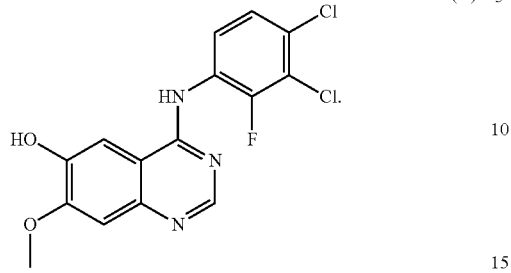
(V)
* * * * *